United States Patent [19]
Hermonat et al.

[11] Patent Number: 6,153,436
[45] Date of Patent: Nov. 28, 2000

[54] METHOD OF GENE DELIVERY USING WILDTYPE ADENO ASSOCIATED VIRAL (AAV) VECTORS WITH INSERTIONS

[75] Inventors: Paul L. Hermonat; J. Gerald Quirk, both of Little Rock; Brian Bishop, Harrison; Han Li, Little Rock, all of Ark.

[73] Assignee: The Board of Trustees of the University of Arkansas, Little Rock, Ark.

[21] Appl. No.: 09/004,877

[22] Filed: Jan. 9, 1998

Related U.S. Application Data

[60] Provisional application No. 60/035,304, Jan. 10, 1997.

[51] Int. Cl.$^7$ .................................................. C12N 15/86
[52] U.S. Cl. ...................... 435/456; 435/235.1; 435/440; 435/455; 435/325; 424/93.2
[58] Field of Search ................................ 435/440, 320.1, 435/235.1, 455, 456; 514/44; 424/93.2

[56] References Cited

U.S. PATENT DOCUMENTS 5,139,941  8/1992  Muzyczka et al. .................. 435/172.3

OTHER PUBLICATIONS

Walz et al. Adeno–associated Virus Sensitizes HeLa Cell Tumors to Gamma Rays. Journal of Virology, vol. 66, No. 9, pp. 5651–5657, Sep. 1992.

Barinaga, M. Ribozymes: Killing the Messenger. Science, vol. 262, pp. 1512–1514, Dec. 03, 1993.

Roush, W. Antisense Aims for a Renaissance. Science, vol. 276, pp. 1192–1193, May 23, 1997.

Dong et al. Quantitative Analysis of the Packaging Capacity of Recombinant Adeno–Associated Virus. Human Gene Therapy, vol. 7, pp. 2101–2112, Nov. 10, 1996.

Halbert et al. Adeno–Associated Virus Vectors Transduce Primary Cells Much Less Efficiently than Immortalized Cells. Journal of Virology, vol. 69, No. 3, pp. 1473–1479, Mar. 1995.

Henig et al. Update on Clinical Trials of Cystic Fibrosis. Current Opinion in Pulmonary Medicine, vol. 3, pp. 404–409, 1997.

Orkin et al. Report and Recommendations of the Panel to Assess the NIH Investment in Research on Gene Therapy. Distributed by the National Institutes of Health, Bethesda, MD, www.nih.gov, Dec. 07, 1995.

Marshall, E. Gene Therapy's Growing Pains. Science, vol. 269, pp. 1050–1055, Aug. 25, 1995.

Verma et al. Gene Therapy–Promises, Problems, and Prospects. Nature, vol. 389, pp. 239–242, Sep. 18, 1997.

*Primary Examiner*—Deborah J. Clark
*Attorney, Agent, or Firm*—Benjamin Aaron Adler

[57] ABSTRACT

The present invention provides a method of human gene therapy using AAV vectors with essentially wildtype phenotype. Genes of 900 bases or less can be inserted into wildtype AAV and still allow the resulting vector to have a largely wildtype phenotype. For example, several antisense genes could be inserted and still allow packaging. Such wildtype vectors have several advantages. First, high titers of such vectors is easy to accomplish. Second, the vectors, since they include the Rep78 gene, integrate specifically into human chromosome 19. Third, such vectors, being wildtype, spread after their initial introduction. Another method for use of large wildtype AAV genomes is as complementors for fully defective AAV vectors. Such complementors can be delivered by virus infection and, be introduced easily into 100% of the cells used to produce virus. Viral infection is superior to synthetic techniques for introducing DNA into tissue culture producer cells. When large essentially wildtype AAV complementor virus are used in conjunction with AAV vector virus allowing for the introduction of both vectors into all cells, high titers of recombinant AAV virus is achieved.

5 Claims, 15 Drawing Sheets

HeLa cells
1st plate: ins96+0.6　ins96+0.7　ins96+0.8　ins96+0.9　ins96+1.0　null dsm>
ssm>

2nd plate: ins96+0.6　ins96+0.7　ins96+0.8　ins96+0.9　ins96+1.0　null dsm>
ssm>

METHOD OF GENE DELIVERY USING WILDTYPE ADENO ASSOCIATED VIRAL (AAV) VECTORS WITH INSERTIONS

CROSS-REFERENCE TO RELATED APPLICATION

This application is a continuing application of provisional application U.S. Ser. No. 60/035,304, filed Jan. 10, 1997, now abandoned.

FEDERAL FUNDING LEGEND

This invention was produced in part using funds obtained through grant CA50551 from the National Cancer Institute. Consequently, the federal government has certain rights in this invention.

BACKGROUND OF THE INVENTION

1. Field of the Invention

The present invention relates generally to a method of human gene therapy using an adeno-associated viral (AAV) vector. More specifically, the present invention relates to the use of an AAV More specifically, the present invention relates to the use of an AAV vector having an essentially wildtype phenotype as a human gene therapy vector for expressing a foreign, therapeutic gene of interest having a size of up to 1000 nucleotide base pairs. Additionally, the engineered essentially wildtype AAV vectors may be used as complementors in a method for generating defective AAV vectors.

2. Description of the Related Art

Adeno-associated virus is a helper-dependent human parvovirus which is able to infect cells latently by chromosomal integration. Various studies from 1970 to 1986 demonstrated that 15–30% of immortalized cells could be infected latently with wildtype AAV, and that the AAV genome was chromosomally linked (Hoggan et al., *Proc. 4th Lepetite Colloquium*, Cocoyac, Mexico, North-Holland, Amsterdam, pp 243–49, (1972).; Cheung et al., *J. Virol.* 33:739–48 (1980); Laughlin et al., *J. Virol.* 60:515–21 (1986)). Moreover, a similar ability for integration was demonstrated for recombinant AAV in immortalized tissue culture cells (Hermonat and Muzyczka, *Proc. Natl. Acad. Sci.* 81:6466–70 (1984); and Tratschin et al., *Mol. Cell. Biol.* 5:3251–60 (1985)). In 1988, recombinant AAV transduction of primary hematopoietic stem cells was achieved (LaFace et al., *Virology* 60:483–86 (1988)).

More recently, the preferred site of wildtype AAV integration was demonstrated to be in a region of human chromosome 19 (see, e.g., Kotin et al., *Proc. Natl. Acad. Sci. U.S.A.* 87:2211–15 (1991); Kotin et al., *EMBO. J.* 11:5071–78 (1990); and Samulski et al., *EMBO J.* 10:3941–50 (1991)). Many laboratories have confirmed and extended these data and demonstrated the utility of AAV-based vectors (see, e.g., McLaughlin et al., *J. Virol.* 62:1963–73 (1988); Lebkowski et al., *Mol. Cell. Biol.* 8:3988–96 (1988); Samulski et al., *J. Virol.* 63:3822–28 (1988); Zhou et al., *Exper. Hematol.* 21:928–33 (1993); Flotte et al., *Gene Therapy* 2:29–37 (1995); Russel et al., *Proc. Natl. Acad. Sci. U.S.A.* 92:5719–23 (1995); and Chiorini et al., *Hum. Gene Ther.* 6:1531–1541 (1995)).

In the last year, the mechanism of wildtype AAV integration was shown to involve a complex between chromosome 19 DNA and AAV terminal repeat DNA in the presence of the AAV Rep78/68 protein (Weitzman et al., *Proc. Natl. Acad. Sci. U.S.A.* 91:5808–12 (1994); Giraud et al., *Proc. Natl. Acad. Sci. U.S.A.* 91:10039–43 (1994); and Urcelay et al., *J. Virol.* 69:2038–46 (1995)). The same protein is required for AAV DNA replication (Hermonat et al., *J. Virol.* 51:329–39 (1984); and Tratschin et al.,. *Mol. Cell. Biol.* 5:3251–60 (1985)).

Because of its ability to integrate chromosomally and its nonpathogenic nature, adeno-associated virus (AAV) has significant potential as a human gene therapy vector. However, AAV has a disadvantage as a gene therapy vector due to its limited packaging capacity. Additional disadvantages of recombinant AAV vectors as gene therapy vehicles include the difficulty in producing high virus titers and the vector's inability, after essential genes are deleted, to integrate into chromosome 19 due to the lack of the rep gene (Rep78/68).

The prior art is deficient in that AAV vectors used for gene therapy have not had the ability to integrate into chromosome 19 or to generate high titers of virus. The present invention fulfills this long-standing need and desire in the art.

SUMMARY OF THE INVENTION

The present invention addresses the packaging capacity of large, essentially wildtype AAV genomes. The upper limit of foreign DNA that the AAV vectors of the present invention can package and express efficiently was shown by increasing in size the inserts by increments of one hundred base pairs. It was found that genomes up to about 1000 base pairs larger than wildtype have fully wildtype phenotypes, including characteristic chromosome 19 integration, as long as the insert is ligated into a non-essential portion of the vector. In addition, the AAV vectors used in the method of the present invention also overcome the titer and specific integration problems of prior art AAV vectors. Thus, genes of significant size can be inserted into AAV and still result in a phenotypically wildtype virus. Use of wildtype AAV vectors circumvents the limitations of prior art recombinant, defective AAV vectors. Furthermore, the present invention demonstrates the effectiveness and utility of these essentially wildtype AAV vectors in gene therapy by demonstrating AAV-driven expression of a gene inserted into a non-essential portion of the vector.

One object of the present invention is to provide a method for human gene therapy comprising the step of administering an essentially wildtype adeno-associated viral (AAV) vector to an individual to be treated, wherein said AAV vector has an essentially wildtype phenotype and a therapeutic gene insert of about 1000 nucleotide base pairs or less.

In an embodiment of the present invention, there is provided a method of human gene therapy, comprising the step of administering an adeno-associated viral (AAV) vector in an appropriate carrier to an individual, wherein said vector has an essentially wildtype phenotype and a therapeutic gene insert, and wherein said therapeutic insert may be an antisense gene, a triplex forming oligonucleotide or code for a bioactive protein.

In yet another embodiment of the present invention, there is provided a method of complementing a defective adeno-associated viral vector, comprising the step of: administering an essentially wildtype adeno-associated viral vector to an individual or to a cell culture, wherein said defective AAV vector contains a DNA, such as a therapeutic gene for the purpose of generating virus particles of the defective adeno associated viral vector.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
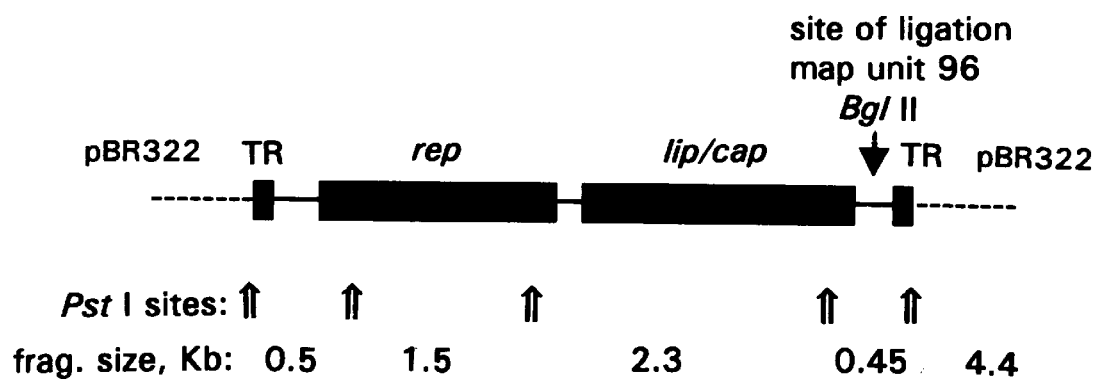
FIG. 1 shows the structure and Pst I map of large AAV genomes. The phenotypic map of AAV is shown at the top with the four phenotypes (TR/ori, rep, lip, cap) labeled (Hermonat et al., J. Virol. 51(2):329–39 (1984)). Also indicated is the position of the Bgl II site at map unit 96 into which foreign DNA was ligated to generate the larger than wildtype AAV vectors referred to in the Examples of this specification. Shown are the Pst I digestion sites within the cloned AAV plasmid ins96 from which the larger than wildtype AAV vectors were generated. The fragment sizes are indicated.

As used herein, the terms "adeno-associated virus" or "AAV" shall mean double-stranded DNA viruses belonging to the family Adenoviridae. As used herein, the term "essentially wildtype adeno-associated virus" shall refer to adeno-associated virus that has a genome containing more than 5 open reading frames, is able to produce high virus titers, can integrate into chromosome 19, and has normal packaging capabilities.

As used herein, the term "essentially wildtype adeno-associated viral vector", or "large essentially wildtype adeno-associated viral genome" shall mean a viral vector or viral genome comprised of the genome of an essentially wildtype adeno-associated virus plus a foreign or therapeutic gene insert of interest. As used herein the term "defective adeno-associated viral vector" shall refer to adeno-associated viral vectors which are missing genes or parts of genes necessary to complete successfully the viral life cycle.

As used herein, the terms "therapeutic gene", "therapeutic DNA", "therapeutic gene insert", "therapeutic gene of interest", "foreign gene", or "foreign gene of interest" shall mean the non-adenoviral DNA that is inserted into an essentially wildtype adeno-associated viral genome to produce an essentially wildtype adeno-associated viral vector for the methods of human gene therapy of the present invention. The therapeutic or foreign DNA insert of interest may code for antisense sequences, triplex forming oligonucleotide sequences, or any bioactive peptide molecule, as long as the insert does not exceed about 1000 nucleotides base pairs. Bioactive molecules include but are not limited to hormones, bioactive peptides, growth factors, trophins, neurotrophins, and neural growth factors, antisense gene, a ribozyme gene, a cytokine gene, an adenovirus gene, a herpes virus gene, papilloma virus gene.

As used herein, the term "pharmacologically acceptable carriers" refers to any number of inactive chemicals that can be used to deliver the essentially wildtype adeno-associated viral vector to the individual to elicit a therapeutic response. A carrier is pharmacologically acceptable if its administration can be tolerated by the recipient human. Such a carrier, along with the essentially wildtype adeno-associated viral vector is said to be administered in a "therapeutically effective amount" if the amount administered is physiologically significant. An agent is "physiologically significant" if its presence results in a change in the physiology of the recipient human. For example, in the treatment of disease, a combination of carrier and essentially wildtype adeno-associated viral vector which relieves or arrests further progress of the disease would be considered both physiologically significant and therapeutically effective.

The present invention is directed to a method for gene therapy in humans comprising administering an essentially wildtype adeno-associated viral (AAV) vector to an individual to be treated, wherein said essentially wildtype adeno-associated vector has a therapeutic gene insert of about 1000 nucleotide base pairs or less.

It is contemplated additionally that such essentially wildtype adeno-associated viral vectors could be used as complementors of defective AAV vectors. In such a case, the method comprises method of complementing a defective adeno-associated viral vector, comprising the step of: administering an essentially wildtype adeno-associated viral vector to an individual or to a cell culture, wherein said essentially wildtype AAV vector contains a DNA insert of a size up to about 1000 nucleotide base pairs, wherein said viral vector remains phenotypically wildtype for the purpose of generating virus particles of the defective adeno associated viral vector.

For both gene therapy and complementation applications, a person having ordinary skill in the art of molecular virology and gene therapy would be able to determine, without undue experimentation, the appropriate dosages and routes of administration of the essentially wildtype AAV vector used in the novel methods of the present invention.

In order to maximize the usefulness of the method of gene therapy of the present invention, the maximum packaging capacity of wildtype adeno-associated virus (AAV) was determined. Altered wildtype AAV genomes were constructed with inserts, said inserts increasing in size by 100 base pairs and ligated at map unit 96. These large wildtype genomes were able to replicate and produce infectious virus at levels slightly reduced, but comparable to wildtype, until the insert size reached 1000 nucleotide base pairs. The data obtained indicated that the maximum effective packaging capacity of AAV with an essentially wildtype phenotype and without deletion of essential viral genes is approximately 1000 base pairs larger than wildtype AAV, or approximately 120% of the size of the wildtype AAV genome. These large, essentially wildtype AAV genomes are able latently to infect the cells by chromosome 19 integration, as does wildtype AAV. Thus, essentially wildtype AAV gene therapy vectors carrying a foreign gene of about 900 base pairs or less can be generated from AAV by ligation into nonessential locations.

The following examples are given for the purpose of illustrating various embodiments of the invention and are not meant to limit the present invention in any fashion:

EXAMPLE 1

Cells and Plasmids

HeLa, SW13, D510 (Detroit 510), and 293 cells were used for the experiments and were grown in Delbecco's Modified Eagles Medium (DMEM) with 7% fetal bovine serum, penicillin and streptomycin.

To generate the AAV plasmids, "100 bp DNA ladder" marker DNA was purchased from GibcoBRL (catalog #15628), agarose gel electrophoresed, and the 600, 700, 800, 900, and 1000 bp fragments were cut out of the gel and isolated by the Quiex DNA isolation kit (Quiagen). Each of the isolated fragments was ligated into the Bgl II site of the ins96 AAV vector using BamH I linkers to generate AAV vectors ins96+0.6, ins96+0.7, ins96+0.8, ins96+0.9, and ins96+1.0. Ins96-λ-F has been described previously and contains a 1.1 kb λ phage DNA fragment ligated into the above-mentioned Bgl II site. The plasmid pSM620 has been previously described (Samulski et al., *Proc. Natl. Acad. Sci. USA*, 79:2077 (1982)). The 960 bp fragment containing the Neomycin (Neo) resistance gene was ligated into the BglII site of ins96 to generate ins96-0.9Neo. When G418 selection was required, G418 was added two days after infection at a concentration of 300 μg/ml for three days, followed by 200 μg/ml for the next three days, and 100 μg/ml thereafter.

EXAMPLE 2

Methods for Analysis of DNA Replication and Virus Production

To investigate the maximum packaging capacity of adeno-associated virus (AAV), the altered wildtype AAV genomes were constructed with inserts and were DEAE/dextran transfected into Adenovirus Type2-infected tissue culture cells. In the case of transfections with ins96-0.9Neo, the virus stocks were treated with deoxyribonuclease I to eliminate the possiblity of extraneous DNA carryover artifacts. One ins96-0.9Neo virus stock was generated by tfx20 (Promega) lipofection, using the manufacturers directions and 293 cells. Half of the transfected cells were analyzed for AAV DNA replication by Southern blot analysis, and the other half of cells and the medium was harvested to be used as a putative virus stock. The putative stocks were tested for infectious virus by infecting a second plate of cultured cells.

Specifically, 1 μg of AAV plasmid was DEAE/dextran transfected as described previously by Hermonat and Muzyczka, (1984), cited supra. The cells were then infected with Adenovirus Type2 at a multiplicity of infection (MOI) of 5. At 36–48 hours the medium and one half of the cells were harvested. The remaining cells of the first plate were analyzed by low molecular weight Hirt DNA extraction (Hirt, *J. Molec. Biol.* 26:365–69 (1967)) and Southern blot analysis (Southern, *J. Molec. Biol.* 98:502–17 (1975)), probing with $^{32}$P-labeled AAV DNA or the 100 base pair ladder DNA to observe viral replication. The harvested cells were left in suspension in DMEM (10 mls), freeze/thawed three times, treated with deoxyribonuclease I at 0.01% for 2 hours to overnight, and heated to 56° C. for 30 minutes to inactivate the Ad helper. One third (33%) of the suspension (putative virus stock) was then added to a second plate of tissue culture cells which were infected subsequently with Adenovirus Type2 at an MOI of 5. At 36–48 hours, the second plates of cells were Hirt DNA extracted to assess virus production. Ten percent of the extracted DNA from both the first and second plates were agarose gel electrophoresed, Southern blotted, and probed with $^{32}$P-labeled AAV DNA, $^{32}$P-100 base pair ladder DNA or $^{32}$P-Neo DNA probes.

EXAMPLE 3

Construction of latently infected cells $1\times10^3$ HeLa or D510 cells were infected with $1\times10^6$ infectious units of ins96-0.9virus. The cell cultures were then grown for 4 to 5 weeks, with at least three cell splits/replatings.

EXAMPLE 4

PCR Amplification and Dot Blot Hybridization Analysis

Three different PCR procedures, amplifying either the AAV rep gene or the AAV TR-chromosome 19 junction, were performed on DNA from the D510 cells described in Example 3. PCR amplification and dot blot hybridization analysis for AAV rep sequences was performed as described by Han et al. (1996). The primers for PCR amplification of an AAV-chromosome 19 junction have been described by Samulski et al. (1991), cited supra. An additional primer set was designed from the Neo gene sequence. Dot blot hybridization analysis of the PCR amplified AAV-chromosome 19 junction was performed with a probe from the AAV terminal repeat (nucleotides 95–125). The probe for Neo PCR amplification products was a 20 base sequence located between the two primers in the target sequence. Each PCR reaction contained approximately 1 μg of total DNA isolated from the indicated cell. The reaction buffer, with and without pSM620 (cloned wild type AAV in 1 μg of HeLa cell genomic DNA), served as the positive and negative controls, respectively, for the AAV rep amplifications. One tenth volume of the PCR product was then denatured, fixed to a nylon membrane and hybridized with appropriate internal $^{32}$P-probes (sequences located between the two primers).

EXAMPLE 5

Reverse Transcriptase primer extension and S1 nuclease protection analysis

Mapping of the 5' ends of the RNAs was carried out by two assay systems, reverse transcriptase primer extension and S1 nuclease protection. The primer extension analyses were carried out as described (Hermonat et al., *EMBO J.* 7:2815 (1988)), with the exception that different primers were used. Primer "Neo" (5'-TCATAGCCGAATAGCCTCCTC) (SEQ ID No. 1) was complementary to the RNA sequences at the 5' end of the Neo gene, while primer "3958" (5'-ATCTGCGGTAGCTGCTTGTC) (SEQ ID No. 2) was complementary to RNA at the 5' end of the X open reading frame (see FIG. 15). Total RNA was isolated from bulk, G418 selected, ins96–0.9Neo infected HeLa cells using the Promega RNAgents kit as directed. For S1 nuclease analysis, the probe was generated by single sided PCR. Single stranded, $^{32}$P-labeled probe for the S1 nuclease analysis was generated by single sided PCR amplification as described (Gyllensten et al., *Proc. Natl. Acad. Sci. USA,* 85:7652 (1988)), except that only the $^{32}$P-labeled "3958" primer was used. The 2 kb AatII fragment from the 3' end of the pSM620 plasmid was used as a template to generate the probe from the primer. The resulting 671 base product was gel-purified using the Qiagen-II gel extraction kit. Total RNA (10 µg) was incubated with 100 ng of $^{32}$P-671 base probe plus various levels of S1 endonuclease for 10 minutes. The digested products were then analyzed on an 8 M urea, 7% PAGE gel.

EXAMPLE 6

Demonstration that Large AAV Genomes are able to Effectively Replicate their DNA To define the packaging capacity of the AAV virion, the large essentially wildtype AAV genomes with the inserts described in Example 1 were used. As described in Example 1, the ligated fragments ranged in size from 600 to 1000 base pairs, resulting in AAV vectors ins96+0.6, ins96+0.7, ins96+0.8, ins96+0.9, and ins96+1.0. The Pst I map of the cloned AAV genome is shown in FIG. 1, and an agarose gel analysis of these plasmids, analyzed by Pst I digestion, is shown in FIG. 2.

Figure 2:
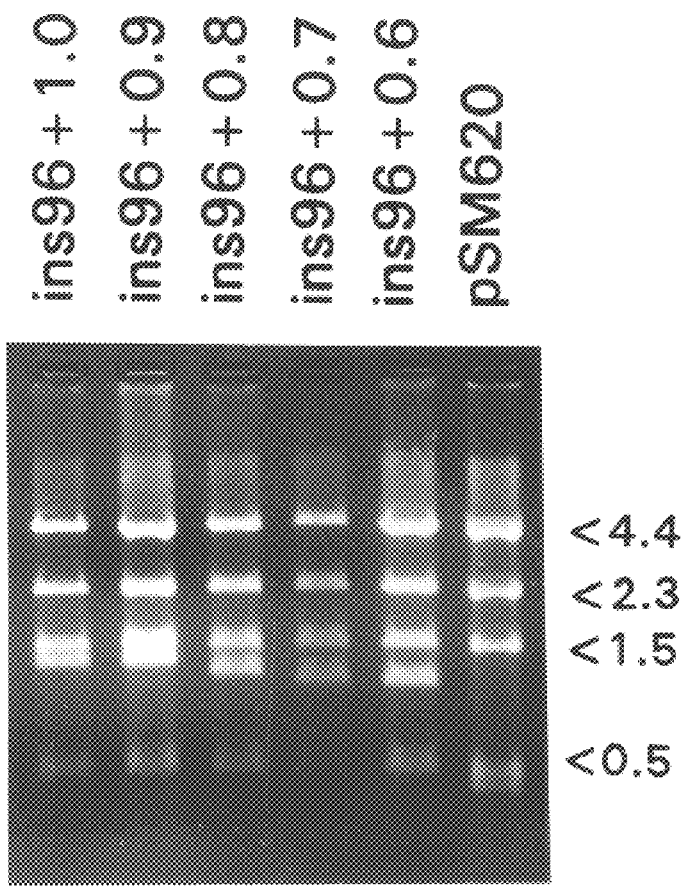
FIG. 2 shows the Pst I analysis of the large AAV genomic plasmids. Shown is a Pst I analysis of the plasmid DNA of larger, essentially wildtype AAV cloned genomes. One μg of each of the indicated AAV plasmids was analyzed via Pst I digestion, agarose gel electrophoresis, and ethidium bromide staining. Note that the Pst I DNA fragment containing the right AAV TR increases in size with the increasing size of the DNA insertion. Originally, the right TR Pst I fragment was 0.45 Kb in size as shown in the pSM620 digestion (pSM620 is fully-wildtype AAV). These altered Pst I fragments increase in size by 0.6 to 1.0 kb, depending upon the size of the DNA ligated into the Bgl II site at map unit 96.

As shown in FIG. 1, the smallest Pst I fragment (≈0.45 kb) encompasses the right AAV terminal region of AAV with the BglII restriction site at nucleotide 4484 (map unit 96). This 0.45 kb fragment increased in size in constructs ins96–0.5 to 1.0, corresponding to the size of the 600–1000 bp fragment which was ligated into it (see FIG. 2). To observe if these altered large AAV genomes were able to replicate, the plasmids were analyzed by Southern blot analysis. Both HeLa and SW13 cells were used in this analysis.

Figure 3:
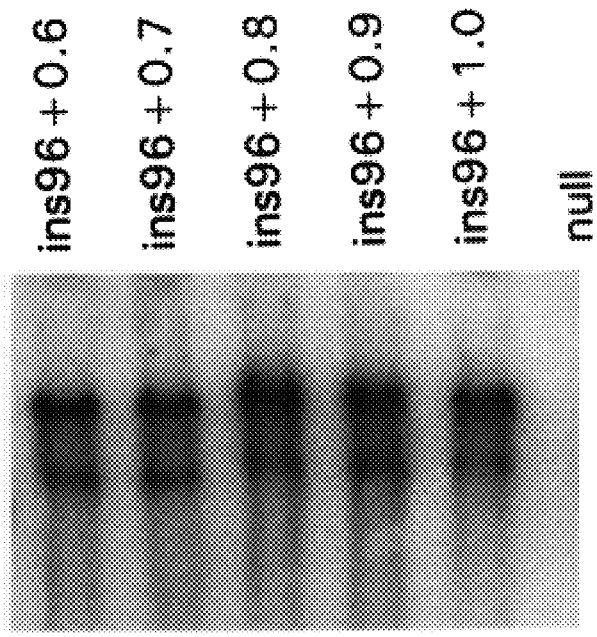
FIG. 3 shows that the Ins96+1.0 is packaged at a lower efficiency than smaller genomes in HeLa cells. Shown is a Southern blot analysis of replicating DNA of the larger than wildtype AAV vectors both in an initial, first DEAE/dextran transfected plate of HeLa cells, and in a second plate into which an aliquot of medium from the first plate (putative virus stock) was transferred. The first plate measures DNA replication and the second plate measures virus production by the level of DNA replication. Note that all the AAV plasmids were able to replicate in the first plate; however, the replication of the ins96+1.0 vector was decreased significantly. This is evident in the second plate where the apparent maximum packaging capacity of the AAV virion was exceeded ("dsm" indicates double stranded monomer DNA, and "ssm" indicates single stranded monomer length DNA).
Figure 3:
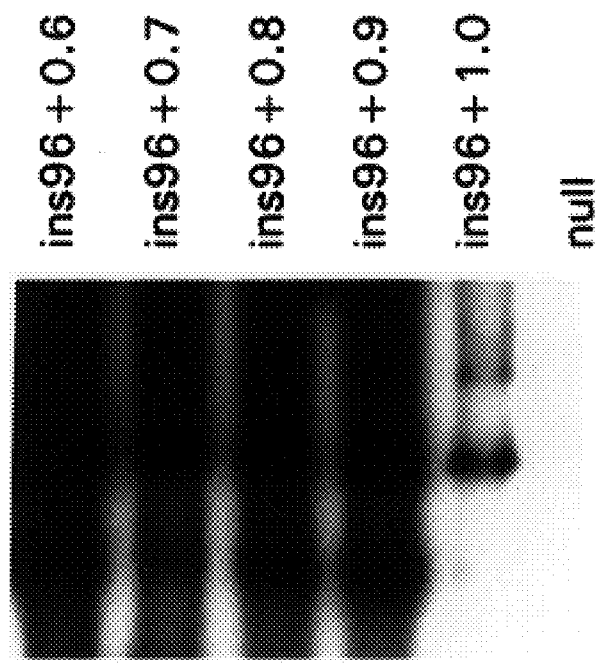
Figure 4:
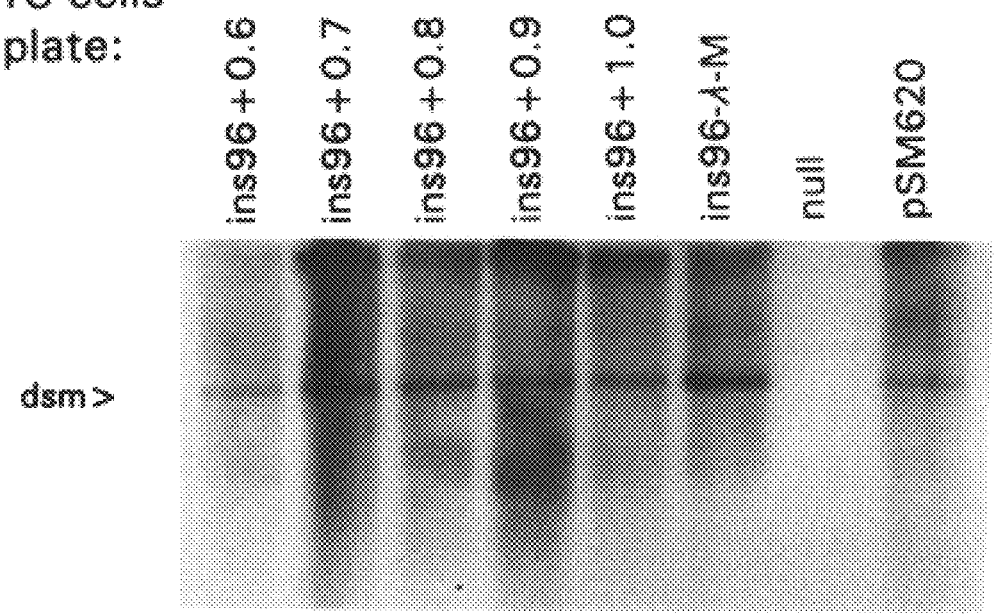
FIG. 4 shows that the Ins96+1.0 is packaged at a lower efficiency than smaller genomes in SW13 cells. An additional packaging experiment was carried out in a similar manner as those experiments described in FIG. 3, except that SW13 cells were used and two additional AAV vectors, ins96-λ-M (1.1 Kb larger than wildtype) and pSM620 (wildtype), were transfected as controls. The results were similar to those results obtained in HeLa cells (FIG. 3). Note that all the AAV vectors were able to replicate in the first plate; however, ins96+1.0 replication was reduced significantly, indicated by the lack of infectious virus in the second plate. There were a few faint bands in the ins96-λ-M and null lanes of the second plate; however, these bands were likely non-specific bands caused by contaminating high molecular weight genomic DNA and/or incomplete washing of the hybridization membrane. These bands were not observed in repeat experiments.
Figure 4:
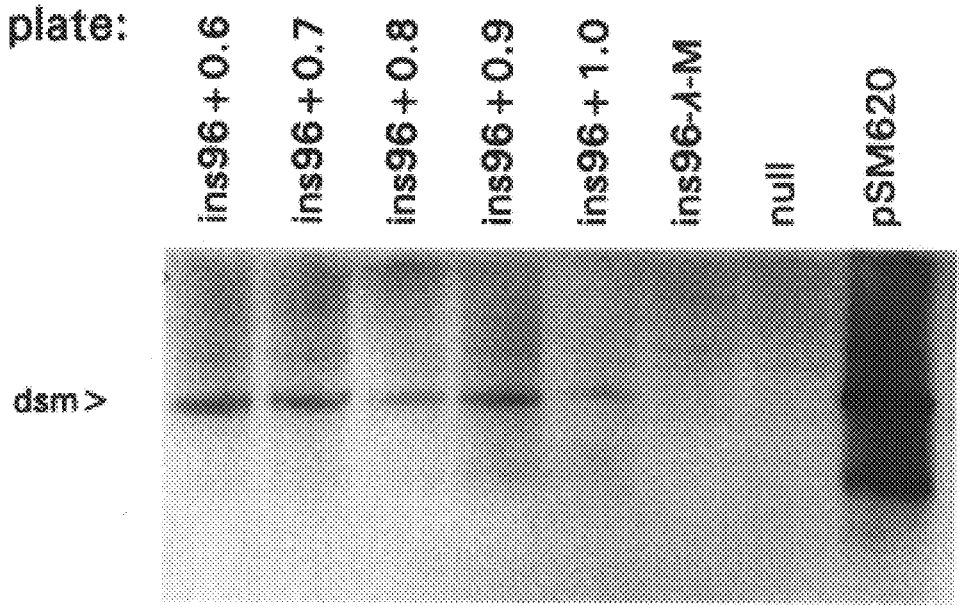
Figure 5:
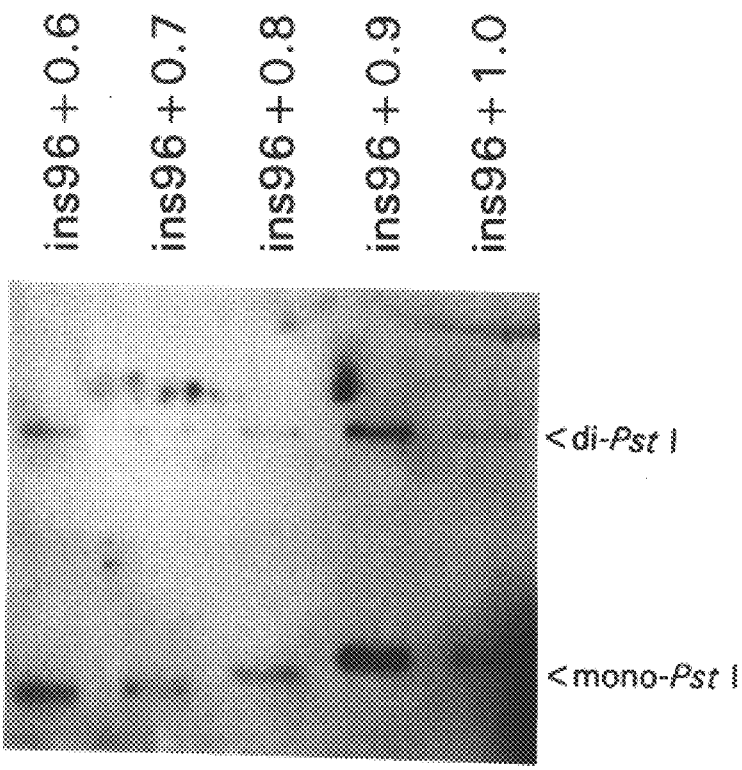
FIG. 5 shows the size analysis of the replicating DNA of the large AAV genomes. Shown is a Pst I analysis of replicating (Hirt) DNA from the first plate described above and shown in FIG. 3. After digestion, the DNA was Southern blotted and probed with $^{32}$P-labeled 100 bp ladder DNA. With this probe, only the altered right Pst I fragment is viewed. Indicated are the monomer- and dimer-size (from tail-to-tail dimers) of Pst I fragments which contain the inserts. Note that the Pst I fragments increase in size corresponding to the size of the insert, with ins96+0.6 giving the smallest, and ins96+1.0 giving the largest sized products. Also note that deleted fragments are not visible, indicating that recombination and elimination of the 100 base pair repeats is not taking place at significant levels.

As shown in the top (first plate) of FIG. 3, all of the large ins96 genomes were able to replicate at comparable levels. As shown in the top (first plate) of FIG. 4 using SW13 cells and using total AAV DNA as $^{32}$P-labeled probe, all of the large ins96 genomes were able to replicate at levels comparable to unaltered wildtype AAV (pSM620). In FIG. 5, the replicating DNAs from the same Hirt DNAs of FIG. 3 were further analyzed by Southern blot analysis after Pst I digestion ($^{32}$P-labeled 100 bp ladder marker DNA as the probe) to better observe the size differences of the AAV genomes. There was a corresponding, ascending increase in size of the replicated DNA, comparable to an increase in size of the inserted DNA. No smaller, deleted, Pst I fragments were observed below the full length bands, indicating that significant deletions of the 100 bp marker DNA inserts are not taking place.

EXAMPLE 7

AAV Genomes 1.0 Kb Larger Than Wildtype are Inefficient at Generating Infectious Virus Particles The same large AAV genomes were assayed for their ability to generate infectious virus. This was done by transferring aliquots of putative virus stock from the first transfected plate into a second plate, infecting with Adenovirus Type2, and analyzing for AAV DNA replication by Southern blot analysis. As shown in the bottom of FIGS. 3 and 4 (second plate), the large AAV genomes, ins96+0.6, ins96+0.7, ins95+0.8, and ins96+0.9, were able to produce virus effectively as indicated by the DNA replication in the second plate. In contrast, ins96+1.0 was significantly lower in virus production in both HeLa and SW13 cells. Ins96-X-M, which is 1.1 Kb larger than wildtype, was very inefficient in generating infectious virus (see FIG. 4). However, upon very long exposure, it was observed that ins96-λ-M did produce low levels of infectious virus (estimated to be ≈0.1–1% that of wildtype).

EXAMPLE 8

Figure 6A:
FIG. 6A–C shows the latent infection and chromosome 19 integration of the ins96+0.9 virus genome. Panel A shows a Southern blot of Adenovirus Type 2 rescue of HeLa cells latently infected four weeks earlier with ins96+0.9 virus. Panel B shows PCR amplification/dot blot analysis for AAV rep DNA sequences from D510 cells latently infected four weeks earlier with ins96+0.9 virus. Panel C shows PCR amplification/dot blot analysis for AAV-chromosome 19 junction DNA sequences from D510 cells latently infected four weeks earlier with ins96+0.9 virus.

Infectious ins96+0.9 Kb Virus are Able Latently to Infect Cells by Chromosome 19 Integration To determine if large AAV genomes are able to infect cells latently by chromosomal integration, 1×10³ HeLa cells were infected with ins96+0.9 virus stock. The cells were grown to confluence, then passed three times after 1:10 splits. After four weeks of continuous growth, the HeLa/ins96+0.9 cells were infected with adenovirus to rescue any chromosomally integrated ins96+0.9 genomes. The Southern blot analysis of Hirt DNA using $^{32}$P-labeled 100 bp marker probe is shown in FIG. 6A. A significant level of replicating ins96+0.9 DNA is seen. Although it was not demonstrated directly that the ins96+0.9 genome is chromosomally integrated after four weeks of cell growth (and DNA replication), it is not likely that remaining episomal AAV DNA would exist at any significant level. The demonstration of significant ins96+0.9 replicating DNA after Adenovirus Type 2 infection strongly suggests that considerable levels of chromosomal integration has taken place.

EXAMPLE 9

Integration into Chromosome 19

To demonstrate specifically that the ins96+0.9 virus was integrated into human chromosome 19, 1×10³ D510 cells were infected with ins96+0.9 virus stock. The cells were grown to confluence, then passed three times after 1:10 splits. After over four weeks of continuous growth, genomic DNA was isolated and analyzed by two different PCR amplification/dot blot hybridization procedures.

Figures 6B, 6C:
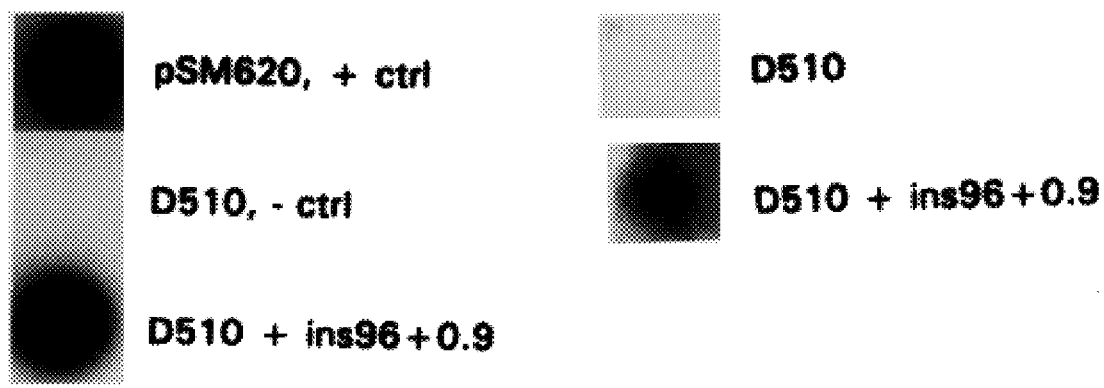

First, shown in FIG. 6B, amplification and hybridization for AAV rep sequences was carried out. D510 cells were infected latently with ins96+0.9 virus as in Example 8. Total cellular DNA was isolated. One µg of the cellular DNA was used for PCR amplification with primers designed to amplify part of the AAV rep gene. One tenth of the PCR product was then dot blotted and probed using a sequence located between the two primers. The D510 cells latently infected with ins96+0.9 virus gave a very strong signal, suggesting chromosomal integration.

Second, to demonstrate chromosome 19 specific integration, amplification and hybridization of the AAV-chromosome 19 junction sequences was carried out (FIG. 6C). One μg of the cellular DNA from B was used for PCR amplification with primers designed to amplify the AAV-chromosome 19 junction within the preferred site of AAV integration. One-tenth of the PCR product was then dot blotted and probed using a sequence located between the two primers within the AAV terminal repeat. The chromosome 19-side primer contains sequences located at the preferred site of AAV integration (Samulski et al., *EMBO J.* 10:3941–50 (1991)). Again, the D510 cells latently infected with ins96+0.9 virus gave a positive signal. These data unambiguously indicate a direct, covalent link between the AAV and chromosome 19 sequences.

EXAMPLE 10

Figure 7:
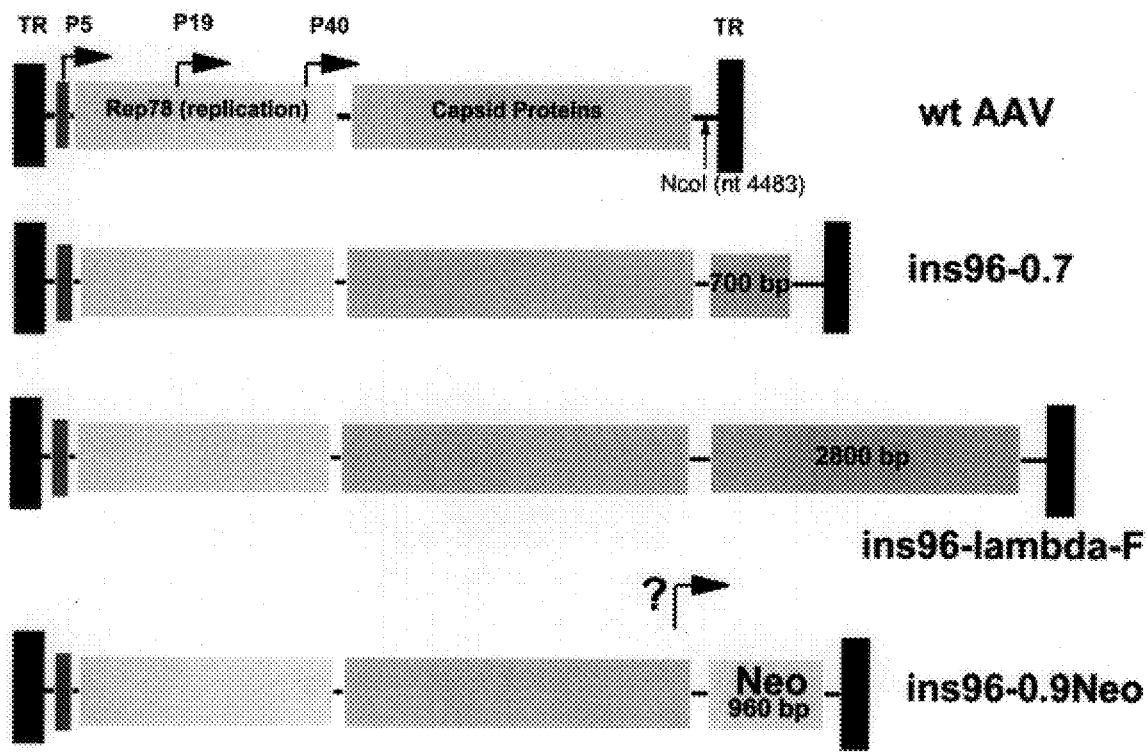
FIG. 7 shows the additional AAV genomes used for transduction of the neo gene. Shown are three genetically wildtype AAV genomes which contain insertions at map unit 96 (NcoI at nt 4460). Important elements are indicated by boxes and include the terminal repeats, the rep, lip/cap, and "X" open reading frames. Ins96–0.7, ins96–0.9Neo, and ins96-lambda-F are 700, 960 and 2,800 bases larger than wildtype in size.

A large AAV genome, ins96–0.9Neo, containing the neomycin resistance gene ligated at map unit 96. is able to effectively replicate its DNA and generate infectious virus To further study the packaging capacity and utility of wildtype-plus AAV gene therapy vectors, the 960 base Neo gene was ligated into the BglII site (at nt 4483, a nonessential location) of ins96 to generate ins96–0.9Neo. Ins96 is a genetically and phenotypically wildtype AAV genome. FIG. 7 displays the positioning of this insert relative to important AAV elements. The ability of ins96–0.9Neo to replicate and generate infectious virus was then analyzed in a "2 plate" assay and compared to pSM620, ins96–0.7, and ins96-lambda-F. The virus stock produced in the first plate was treated with deoxyribonuclease I before addition to the second plate to prevent any artifactual signals due to input DNA carryover.

Figure 8:
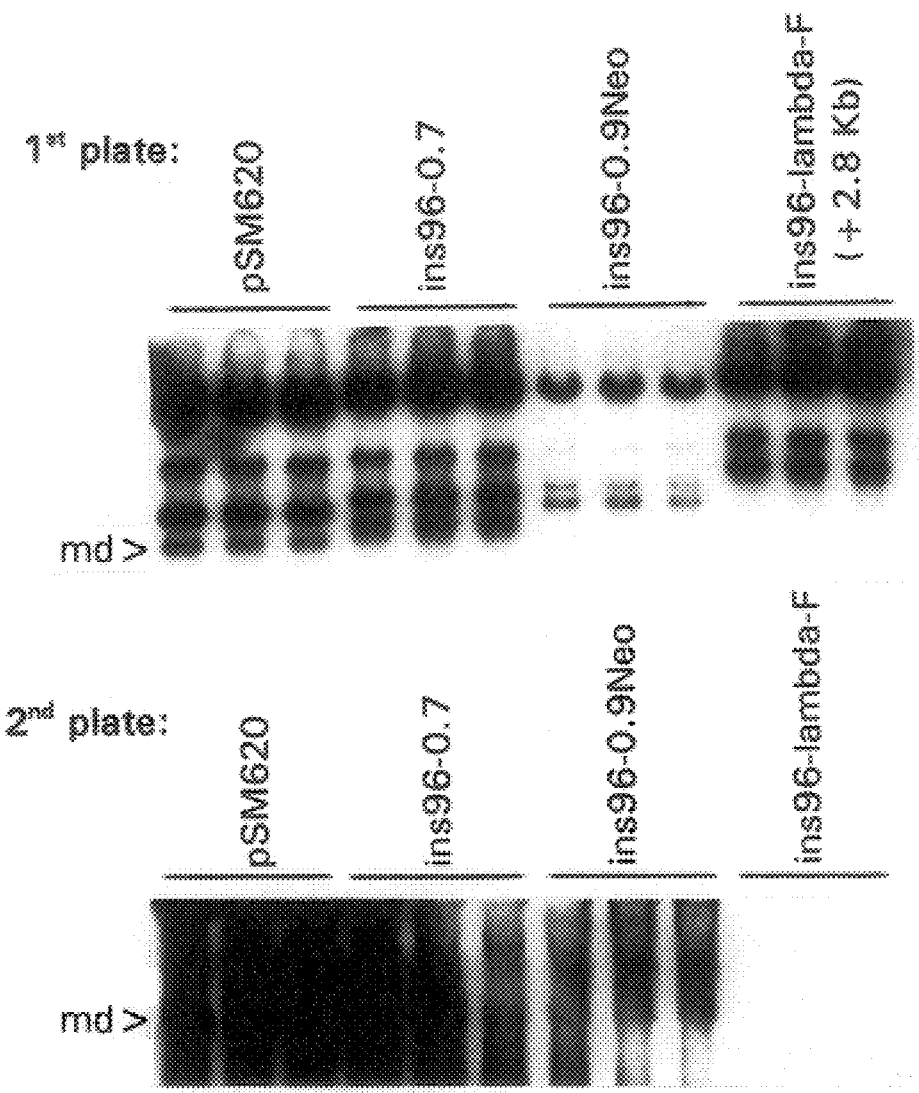
FIG. 8 shows that the ins96–0.9Neo genome is able to replicate and produce infectious virus. Shown are two Southern blots of Hirt extracts. The top "1st plate" shows the Southern blot from SW13 cells DEAE-dextran transfected with the indicated AAV plasmids. The transfections were done in triplicate. At 36 hours post-transfection, one quarter of the Hirt DNA extractions from these cells were agarose gel electrophoresed, Southern blotted and probed for AAV sequences. Note that all of the AAV constructs were able to replicate in the 1st plate. Half of the cells from the 1st plate and the accompanying medium were freeze thawed three times, treated with deoxyribonuclease I, heated to 56° C. to kill the Ad, and an aliquot (1 ml) transferred to a second plate of SW13 cells which were subsequently infected with Ad. At 36 hours post-infection, "2nd plate" Hirt DNA extraction and Southern blot analysis was carried out. Note that ins96–0.9Neo was able to produce virus in the 1st plate, and infect and replicate in the second plate, as does wildtype pSM-620 and ins96–0.7 . In contrast, ins96-lambda-F was not able to produce infectious virus in spite of its ability to replicate in the 1st plate.

The results are shown in FIG. 8. In the first plate, all four AAV genomes were able to replicate their DNA. In these lanes, the lower band is the monomer duplex (md) replicative DNA form, because when the membranes are reprobed with $^{32}$P-pBR322 DNA, all bands remain visible except for this lower band. In the second plate, both pSM620 (wildtype) and ins96–0.7 are able to generate infectious virus, consistent with earlier results. In comparison, ins96-lambda-F, while genetically wildtype, does not generate infectious virus as it is too large (7.5 kb in length) to be packaged. Most importantly, ins96–0.9Neo generated significant levels of infectious virus, although at lower levels than normal wildtype pSM620.

Figure 9:
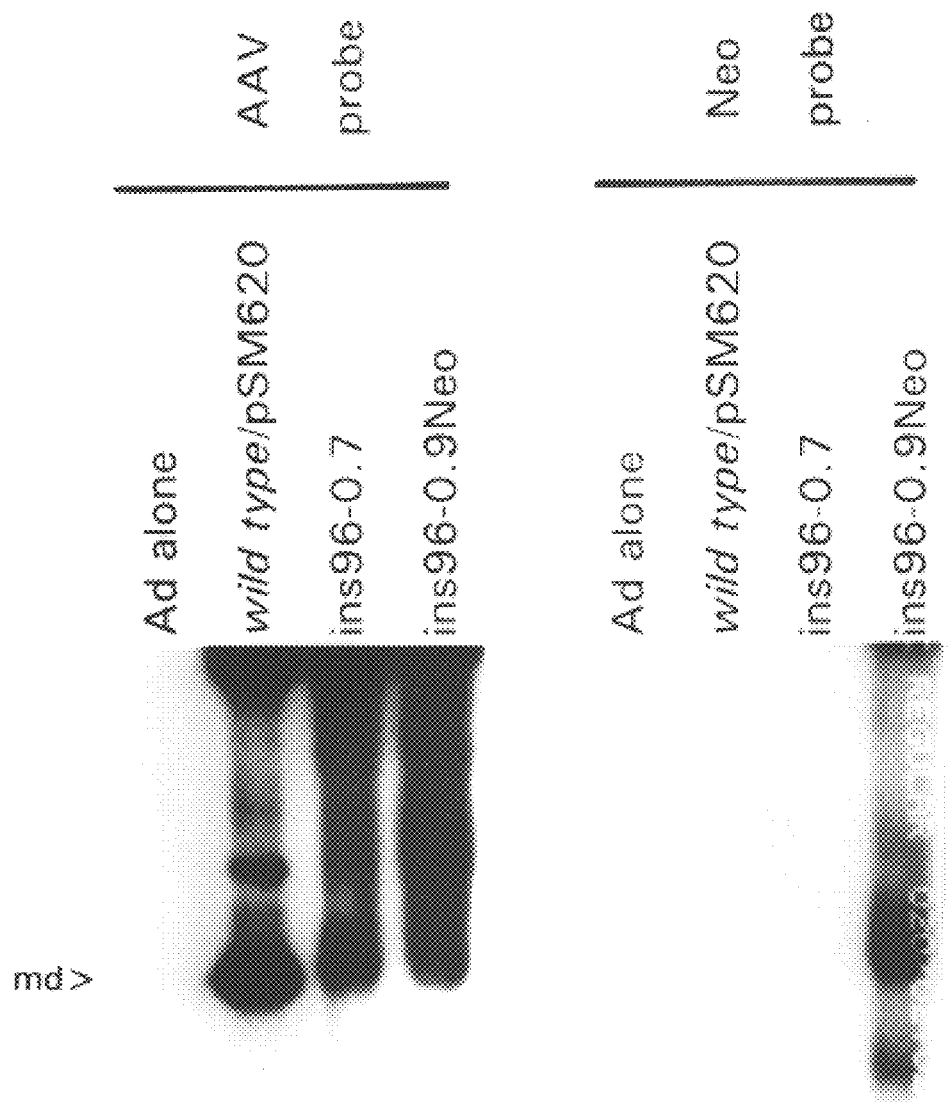
FIG. 9 shows that the Ins96–0.9Neo virus stocks retain the Neo sequences. Shown is a Southern blot of "2nd plate" Hirt extracts of replicating viral DNA from three indicated AAV virus stocks. On the left, the membrane was probed with $^{32}$P-A A V sequences. Note that wildtype, ins96–0.7 and ins96–0.9Neo DNA replication is shown. On the right is the same membrane reprobed with $^{32}$P-Neo after stripping the previous probe. Note that only the ins96–0.9Neo lane gives a positive signal.

To verify that, in fact, the ins96–0.9Neo virus stock contained the Neo gene, a second plate analysis membrane was probed first with $^{32}$P-AAV DNA, then the membrane was stripped (by incubation in 90° C. water) and reprobed with $^{32}$P-Neo DNA. The results are shown in FIG. 9. Note that all three AAV viruses are shown replicating in the second plate using the AAV probe. However, only ins96–0.9Neo is shown when probed with Neo. In one instance of generating ins96–0.9Neo, two closely sized monomer duplex DNAs were visible using the $^{32}$P-AAV probe. When the membrane was stripped and reprobed with $^{32}$P-Neo probe, only the larger band is favorably targeted by this probe. This data suggested that a naturally occurring deletion had taken place within the Neo sequences. Alternately, this species could be contaminating wild type AAV, however, this has not been a significant problem in the art. Such naturally occurring deletions have been seen before in large wild type-plus AAV genomes such as ins96-lambda-M.

Figure 10:
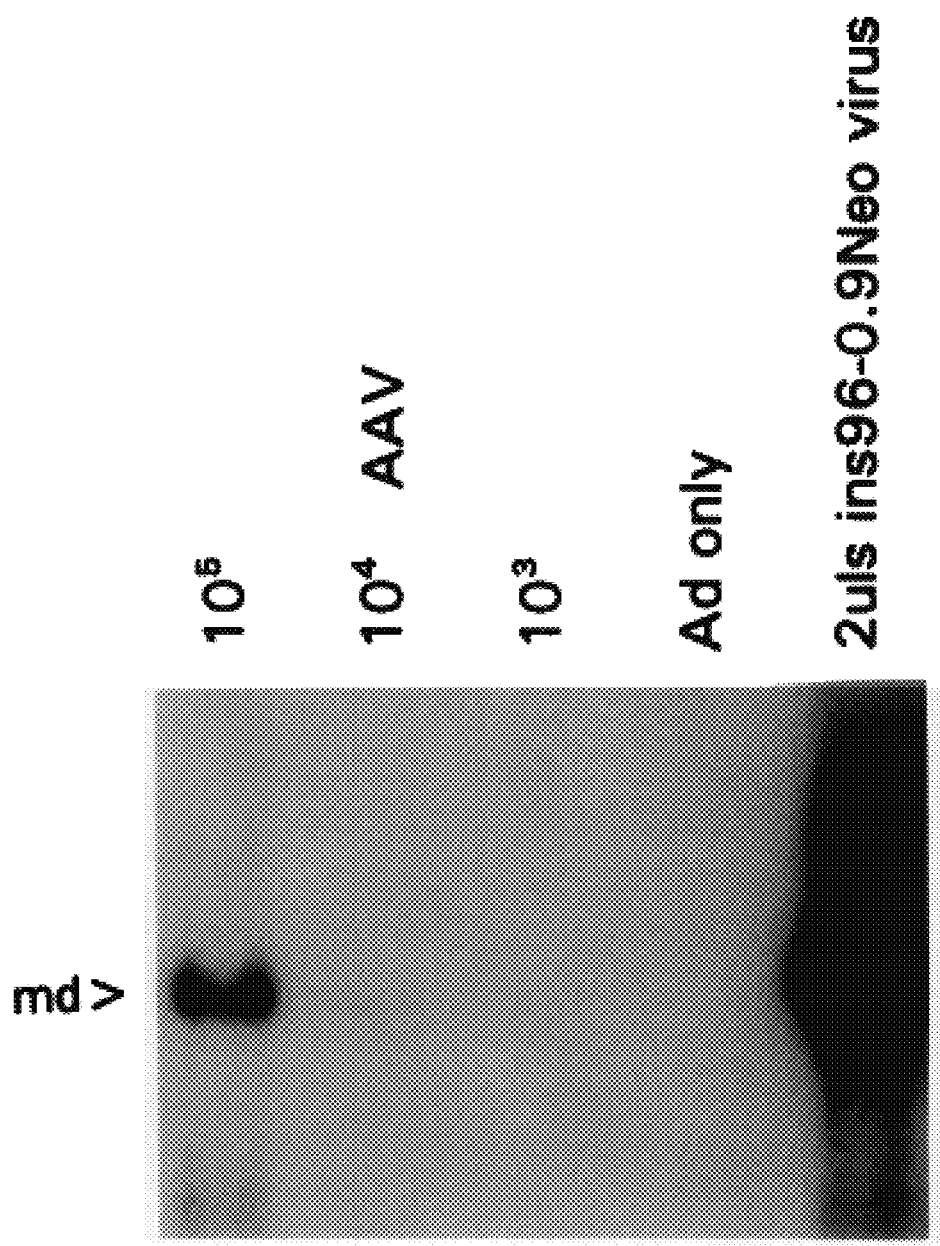
FIG. 10 shows the titering of ins96–0.9Neo virus stocks. Shown is a Southern blot of "2nd plate" Hirt extracts from infection of known amounts of titered AAV virus or 2 μl of an ins96–0.9Neo virus stock. This stock was prepared by tfx 20 (Promega) lipofection of 1 μg of ins96–0.9Neo plasmid onto a 10 cm plate of Ad infected 293 cells. The membrane was probed with $^{32}$P-A A V sequences. Note that there are two monomer duplex bands located close together. From this analysis, it was estimated that the ins96–0.9Neo virus stock was approximately $10^9$ infectious units/ml.

The titer of one ins96–0.9Neo virus stock, prepared by tfx 20 (Promega) lipofection of 1 μg of ins96–0.9Neo plasmid onto a 10 cm plate of 293 cells, was also determined by comparing DNA replication of known amounts of titered AAV virus. The results are shown in FIG. 10, and show that the titer of this particular ins96–0.9Neo virus stock was approximately $10^9$ infectious units/ml without concentrating the virus. This titer is comparable to that of wildtype AAV generated by DEAE-dextran transfection of pSM620. However, stocks of ins96–0.9Neo generated by DEAE-dextran transfection were highly variable and ranged from $10^{6-8}$/ml, seemingly depending upon the weather.

EXAMPLE 11

Ins96–0.9Neo virions are able to stably transduce HeLa cells to G418 resistance and integrate into chromosome 19-S1

Figure 11:
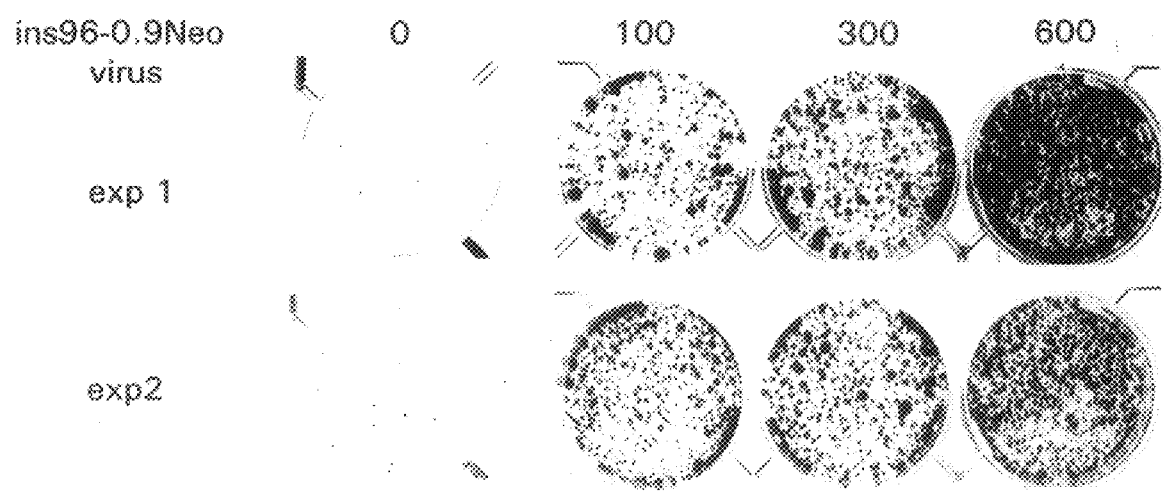
FIG. 11A–C shows the transduction of HeLa cells with ins96–0.9Neo virus. Shown are two transduction experiments in which 6 well plates of D510 cells were infected with ins96–0.9Neo virus and selected with G418. Note that increasing amounts of ins96–0.9Neo virus result in increasing numbers of G418 resistant colonies.

It was next determined whether ins96–0.9Neo virus were able to transduce and convert D510 cells to G418 resistance. Initially, it was considered that such an outcome was unlikely because no dedicated promoter was included with the inserted Neo gene. In the initial experiments with this virus, it was noted that the cells would live considerably longer compared to uninfected controls, yet these cells would eventually die. Thus, it was speculated that the Neo gene might be expressed, but only at a low level. Finally, a G418 selection scheme was arrived at in which G418 selection started at 2 days post-infection at 300 μg/ml for the first 3 days, 200 μg/ml for the next 3 days, and then 100 μg/ml thereafter. Shown in FIG. 11 are two transduction experiments in which 6 well plates of HeLa cells at 10% confluence were infected with the indicated amount of ins96–0.9Neo virus stock ($\approx 10^6$ IU/ml). Selection with G418 was initiated at 2 days post-infection. As can be seen, G418 resistant cells resulted from ins96–0.9Neo virus infection, and the appearance of G418 resistant colonies was dosage dependent.

Figure 12A:
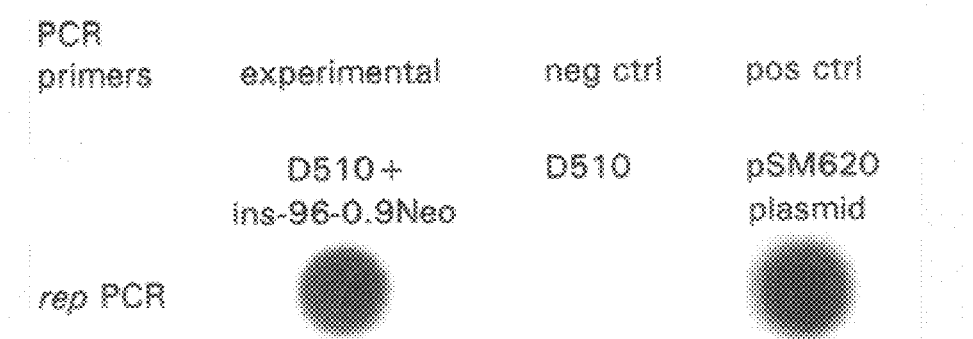
FIG. 12 shows the PCR/dot blot analysis of D510 cells transduced with ins96–0.9Neo virus. Genomic DNA from bulk selected D510 cells which had been transduced with ins96–0.9Neo virus was analyzed by three different PCR primer/probe sets for AAV rep, S1-TR junction, and Neo DNAs. Panel A shows an analysis for rep gene sequences within the transduced cells. Note that DNA from the D510/ins96–0.9Neo cells resulted in a positive signal, while DNA from parental D510 cells did not. The plasmid pSM620 served as a positive control. Panel B shows an analysis for chromosome 19 S1-AAV TR junction sequences within the transduced cells. Note that DNA from the D510/ins96–0.9Neo cells resulted in a positive signal while DNA from parental D510 cells did not. DNA from D510 cells latently infected with ins96–0.9Neo served as a positive control. Panel C shows an analysis for Neo gene sequences within the transduced cells. Note that DNA from the D510/ins96–0.9Neo cells resulted in a positive signal while DNA from parental D510 cells did not. The plasmid ins96–0.9Neo served as a positive control.
Figure 12B:
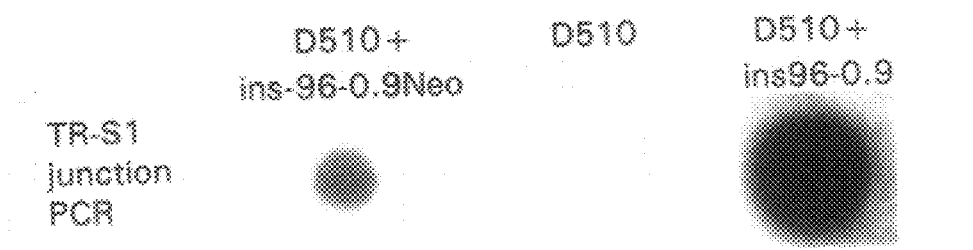
Figure 12C:
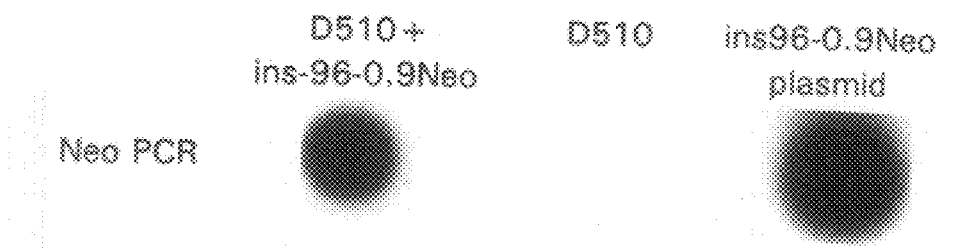

The genomic DNA of D510 cells, which had been transduced with ins96–0.9Neo virus and G418 selected, was examined for ins96–0.9Neo DNA. First, PCR amplification and dot blot hybridization analysis for AAV rep sequences was undertaken. As shown in FIG. 12A, such sequences were present in the ins96-Neo infected/G418 selected D510 cells. Second, in FIG. 12B, to observe chromosome 19 S1 specific integration, PCR analysis and dot blot hybridization was undertaken using one AAV TR primer sequence, one S1 primer sequence and an internal probe also of AAV TR sequences. By this analysis, ins96–0.9Neo was clearly stably transducing cells by chromosomal integration and a significant level of this integration was taking place within the S1 sequence of chromosome 19. Finally, a similar analysis was undertaken for the presence of the Neo gene, and again such sequences were found as shown in FIG. 12C.

EXAMPLE 12

Figure 13A:
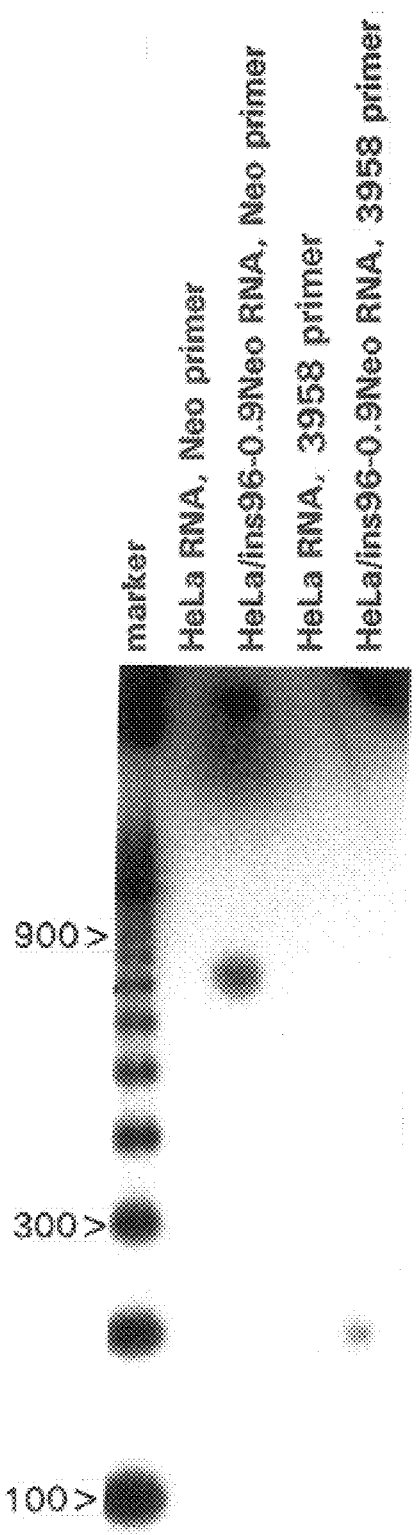
FIG. 13 A–B shows the identification of the p81 promoter by reverse transcriptase primer extension and S1 nuclease protection assays. HeLa cells were infected with ins96–0.9Neo and G418 selected to generate the bulk (multiclonal) cell line, HeLa/ins96–0.9Neo. Total RNA was then isolated from these cells. Panel A shows reverse transcriptase primer extension assay using two different primers, one complementary to the 5' end of the Neo gene ("Neo primer") and one complementary to the 5' end of the X ORF (see FIG. 15). Both primers resulted in products using RNA derived from the HeLa/ins96–0.9Neo cells, but did not give products in RNA from normal HeLa cells. Panel B shows an S1 nuclease protection assay using a probe whose 5' end is the same as the 3958 primer used in panel A. The size of the product is the same as the 3958 primer product in panel A. Thus, the results from both panel A and B support the same location for a new AAV promoter.
Figure 13B:
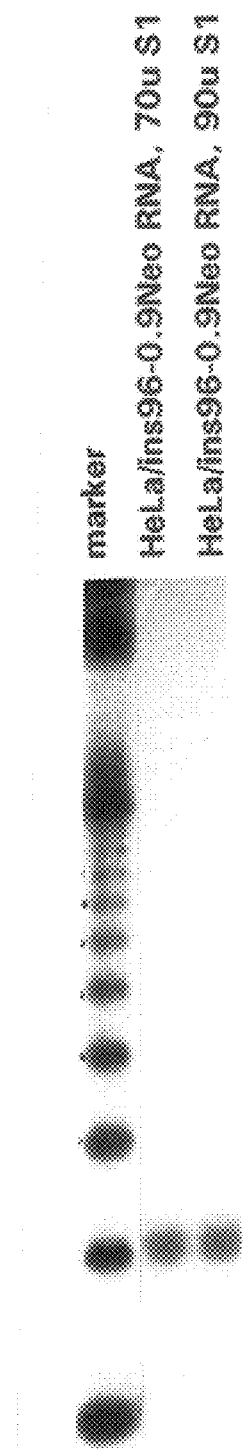
Figure 15:
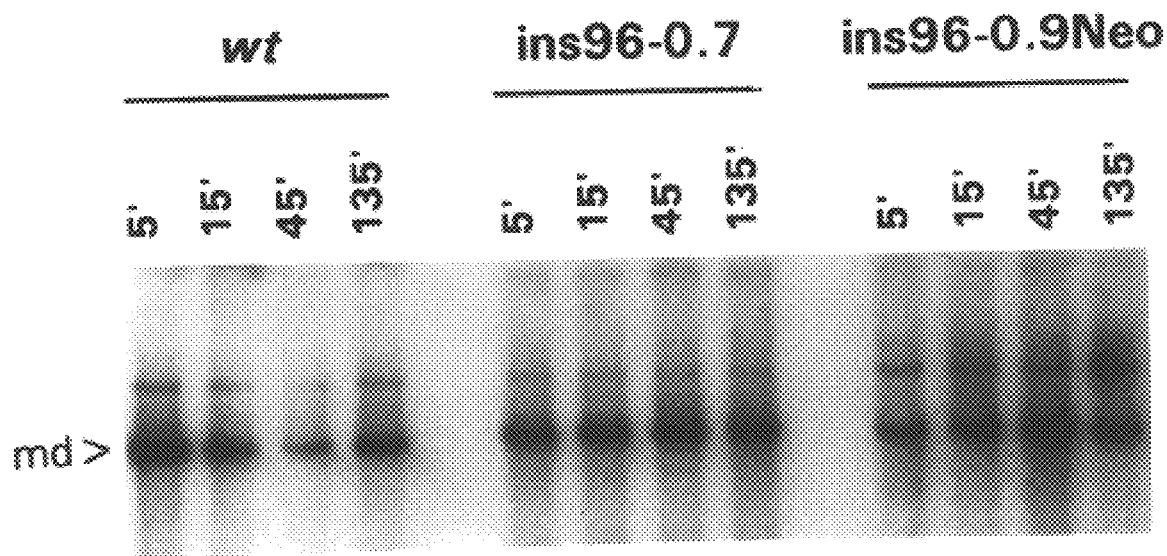
FIG. 15 shows that the Ins96–0.9Neo virus is equally resistant to heat compared to wildtype AAV virus. Aliquots (100 μl) of the indicated virus stocks, which had not been previously heat treated to inactivate Ad, were heated to 56° C. for the indicated time periods. The virus were then used to infect a second plate of adenovirus infected SW13 cells. At 36 hours, Hirt DNA extracts were generated, agarose gel electrophoresed, Southern blotted and probed with $^{32}$P-AAV DNA. None of the virus stocks, including ins96–0.9Neo, appear to lose infectivity with increased time of incubation at 56° C..

Identification of a new AAV promoter. p81, as determined by reverse transcription primer extension (RTPE) using two different primers Because of the unusual expression of the Neo gene at map unit 96, it was desirable to identify the promoter. Total RNA was isolated from ins96–0.9Neo infected-G418 selected HeLa cells, and subjected to RTPE analysis. A primer complementary to the 5' end of the Neo gene was used for this analysis. The results are shown in FIG. 13A. As shown, using the Neo primer, the promoter was located at about 700 bases upstream from the Neo primer. There is no known AAV promoter at this location. However, the AAV genome sequence reveals that there is a significant open reading frame (ORF) just 3' of this location (nt 3922–4388 (Srivastava et al., *J. Virol.* 45:555, (1983); Cassinotti et al., *Virology* 167:176 (1988); Ruffing et al., *J. Gen. Virol.* 75:3385(1994)). FIG. 15 shows the important elements at the 3' end of ins96–0.9Neo, including this ORF named "X". To verify the presence of this promoter, a second RTPE analysis was then undertaken using a primer complementary to the beginning of ORF X. As shown in FIG. 13A, the results show that the primer is located at 220 bases upstream of the ORF "X" primer. The results from both primers are consistent and indicate the the 5' end of the RNA is located between nt 3793–3813.

Figure 14:
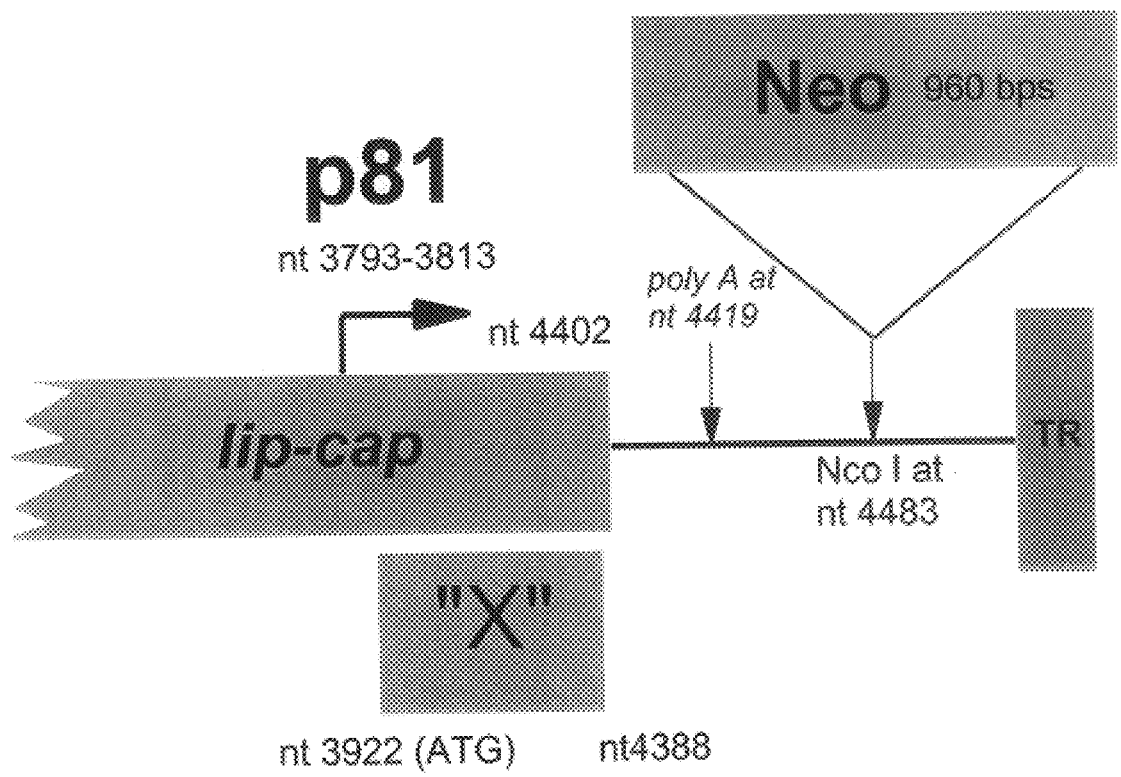
FIG. 14 shows important elements at the 3' end of the AAV genome and the position of the Neo gene insertion. Shown are the lip-cap, Neo, and "X" open reading frames as boxes, one with a ragged edge indicating that it extends farther upstream. The 3' TR of AAV is shown as a vertically high thin box. Also indicated are various important nucleotide sequences, such as the putative TATA box for p81, the NcoI site into which the Neo gene is inserted, as well as others.

EXAMPLE 13
Verification of p81 promoter activity by the S1 nuclease protection analysis In spite of having consistent results from the two reverse transcriptase primer extension analyses, a second assay system, S1 nuclease protection, was used to further verify the presence of the p81 promoter. The DNA probe utilized was generated by single sided PCR using the same primer used to generate the ORF X primer reverse transcriptase primer extension results. As shown in FIG. 14, the length of the product generated by this analysis was equal in length to the ORF X primer reverse transcriptase primer extension analysis. Thus, all three RNA analyses are in agreement and indicate that there is a previously unknown AAV promoter located at map unit 81. In spite of having an intervening gene and polyadenylation signal between the Neo gene and the p81 promoter, Neo was clearly being expressed from this promoter.

EXAMPLE 14
Large wild type plus AAV genomes are heat stable

Because of the increased amount of DNA which is contained in the ins96–0.9Neo virus particle, these virions might be more susceptible to inactivation when compared to smaller AAV genomes. To test this hypothesis, the heat sensitivity of virions of normal length wild type AAV was compared to those of ins96–0.7 and ins96–0.9Neo. Equal aliquots of these virus stocks were subjected to 56° C. for 5, 15, 45, and 135 minutes. The aliquots were then transferred to a second Ad-infected plate for amplification and virion infection level analysis. The results are shown in FIG. 15 and demonstrate that virions of ins96–0.9Neo and ins96–0.7 are equally resistant to heat as normal wild type.

The present invention demonstrates that a wild type-plus AAV vector was able to transduce the 960 base Neomycin resistance gene and thus, wild type-plus AAV vectors are useful for the transduction. Dong et al., 1996 (5) reported that recombinant AAV's maximum packaging capacity is only 500 bases larger than the wild type genome. In contrast, the present invention demonstrates that the maximum packaging capacity of AAV is much larger, approaching 1,000 bases larger than wild type. This large packaging capacity was demonstrated using two different DNA sequences (GibcoBRL 100 base ladder, and the Neo gene). The Dong et al. results are incorrect in regards to determining the maximum packaging capacity of AAV. The natural AAV sequences may have a higher packaging efficiency than unrelated DNA.

The expression of the Neo gene within the ins96–0.9Neo genome was surprising to us. Not only was there no dedicated heterologous promoter placed upstream of the Neo gene, but there was a poly A sequence located just upstream of the Neo I site (FIG. 9). Furthermore, there is no poly A sequence located downstream of the Nco I. Thus the p81 promoter must be sufficiently strong enough and transcript leakage past the poly A signal must be sufficiently frequent enough for expression of Neo to take place. The results from transduction/G418 selection experiments and the reverse transcriptase primer extension experiments using the Neo primer, indicate that this interpretation is correct. Thus, this study has resulted in the discovery of a new AAV promoter (p81) with an initiation site at approximately nt 3793–3813. The identification of P81 was further verified by reverse transcriptase primer extension analysis using an upstream primer to ORF X (primer 3958 ) and by S1 nuclease protection. These data conclusively indicate the presence of this promoter. Furthermore, the presence of this promoter strongly suggests the existence of a new AAV gene from nt 3922–4388 (called "X").

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference. One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of delivering DNA to a target cell, in vitro, using adeno-associated viral vectors, comprising the step of:
    administering an adeno-associated viral vector to said cell, wherein said viral vector retain all adeno-associated viral genomic sequences, wherein said viral vector contains a DNA insert of a size up to about 1000 nucleotide base pairs and wherein said insert is placed after the last coding region of said virus and prior to the right ITR of said virus.

2. The method of claim 1, wherein said DNA insert is less than 900 nucleotide base pairs.

3. The method of claim 1, wherein said DNA insert is inserted into a non-essential portion of the viral vector, wherein non-essential portions do not harbor cis or trans sequences that are required for viral replication or transcription.

4. The method of claim 1, wherein said viral vector integrates into chromosome 19 of said cell.

5. A method of complementing a defective adeno-associated viral vector, comprising the step of:
    administering a defective adeno-associated viral vector to a cell, in vitro; and
    administering a non-defective adeno-associated viral vector to said cell, said non-defective viral vector retaining all adeno-associated viral genomic sequences, wherein said non-defective viral vector contains a DNA insert of a size up to about 1000 nucleotide base pairs and wherein said non-defective viral vector is capable of generating virus particles of the defective adeno-associated viral vector.

\* \* \* \* \*